US011367191B1

(12) United States Patent
Warier et al.

(10) Patent No.: US 11,367,191 B1
(45) Date of Patent: Jun. 21, 2022

(54) ADAPTING REPORT OF NODULES

(71) Applicant: Qure.ai Technologies Private Limited, Mumbai (IN)

(72) Inventors: Prashant Warier, Mumbai (IN); Ankit Modi, Koderma (IN); Preetham Putha, Guntur (IN); Prakash Vanapalli, Vishakapatnam (IN); Pradeep Kumar Thummala, Vishakapatnam (IN); Vijay Senapathi, Kakinada (IN); Kunjesh Kumar, Lumding (IN)

(73) Assignee: Qure.ai Technologies Private Limited

( * ) Notice: Subject to any disclaimer, the term of this patent is extended or adjusted under 35 U.S.C. 154(b) by 0 days.

(21) Appl. No.: 17/457,470

(22) Filed: Dec. 3, 2021

(30) Foreign Application Priority Data

Oct. 7, 2021 (IN) .............................. 202121045732

(51) Int. Cl.
*G06T 7/00* (2017.01)
*G16H 30/40* (2018.01)
*G16H 15/00* (2018.01)
*G06V 10/25* (2022.01)
*G06V 10/764* (2022.01)

(52) U.S. Cl.
CPC ............ *G06T 7/0012* (2013.01); *G06V 10/25* (2022.01); *G06V 10/764* (2022.01); *G16H 15/00* (2018.01); *G16H 30/40* (2018.01); *G06T 2207/10081* (2013.01); *G06T 2207/20081* (2013.01);
(Continued)

(58) Field of Classification Search
CPC ......... G06T 7/0012; G06T 2207/10081; G06T 2207/20081; G06T 2207/20084; G06T 2207/30096; G06V 10/25; G06V 10/764; G16H 15/00; G16H 30/40
See application file for complete search history.

(56) References Cited

U.S. PATENT DOCUMENTS

| 6,738,499 B1 * | 5/2004 | Doi ...................... G06T 7/0012 382/128 |
| 7,783,094 B2 | 8/2010 | Collins et al. |

(Continued)

OTHER PUBLICATIONS

Shen et al., "An Interpretable Deep Hierarchical Semantic Convolutional Neural Network for Lung Nodule Malignancy Classification", arXiv:1806.00712, Jun. 2, 2018, pp. 1-23 (Year: 2018).*

*Primary Examiner* — Nay A Maung
*Assistant Examiner* — Jose M Torres
(74) *Attorney, Agent, or Firm* — FisherBroyles, LLP; Susan M. Oiler (57) ABSTRACT

Disclosed is a system and a method for adapting a report of nodules in computed tomography (CT) scan image. A CT scan image may be resampled into a plurality of slices. A plurality of region of interests may be identified on each slice using an image processing technique. Subsequently, a plurality of nodules may be detected in each region of interest using the deep learning. Further, a plurality of characteristics associated with each nodule may be identified. The plurality of nodules may be classified into AI-confirmed nodules and AI-probable nodules based on a malignancy score. Further, feedback associated with the AI-confirmed nodules and the AI-probable may be received form a radiologist. Furthermore, data may be adapted based on the feedback. Finally, a report comprising adapted data may be generated.

13 Claims, 3 Drawing Sheets

(52) U.S. Cl.
CPC ............... *G06T 2207/20084* (2013.01); *G06T 2207/30096* (2013.01)

(56) References Cited

U.S. PATENT DOCUMENTS

| | | | |
|---|---|---|---|
| 8,488,863 B2 | 7/2013 | Boucheron | |
| 2020/0161005 A1* | 5/2020 | Lyman | G06K 9/6231 |
| 2020/0357117 A1* | 11/2020 | Lyman | G06T 7/0012 |
| 2022/0005586 A1* | 1/2022 | Brynolfsson | G16H 50/20 |

* cited by examiner

ADAPTING REPORT OF NODULES

RELATED APPLICATIONS

This application claims priority to Indian Patent Application No. 202121045732 filed Oct. 7, 2021 in India.

TECHNICAL FIELD

The present subject matter described herein, in general, relates to a system and a method for adapting report of nodules. More particularly, to adapting the report of nodules detected on a Computed Tomography (CT) scan image using artificial intelligence.

BACKGROUND

Typically, medical imaging techniques such as Computed Tomography (CT) scans and X-radiations (X-ray) scans are widely used by a health practitioner to detect lung cancers. It must be noted that an early detection of cancerous nodule is really important. Generally, the health practitioner suggests a patient to go for the CT scans when he/she diagnose a presence of nodule in a chest of the patient. Further, the health practitioner analyses the CT scans and manually identify nodules. However, the manual detection is a time consuming and a cumbersome task. At times, it may happen that the nodules, which are small in size, are missed by the health practitioner.

SUMMARY

Before the present system(s) and method(s), are described, it is to be understood that this application is not limited to the particular system(s), and methodologies described, as there can be multiple possible embodiments which are not expressly illustrated in the present disclosures. It is also to be understood that the terminology used in the description is for the purpose of describing the particular implementations or versions or embodiments only and is not intended to limit the scope of the present application. This summary is provided to introduce aspects related to a system and a method for adapting a report of nodules on a Computed Tomography (CT) scan image. This summary is not intended to identify essential features of the claimed subject matter nor is it intended for use in determining or limiting the scope of the claimed subject matter.

In one implementation, a method for adapting a report of nodules in a Computed Tomography (CT) scan image is disclosed. Initially, a CT scan image of a patient may be received. The CT scan image may be resampled into a plurality of slices. In one aspect, the CT scan image may be resampled using a bilinear interpolation. Further, a plurality of region of interests on each slice may be identified. In one aspect, each region of interest may be identified using an image processing technique. Furthermore, a plurality of nodules in the plurality of region of interests may be detected using the deep learning. Subsequently, a plurality of characteristics associated with each nodule may be determined using the image processing technique. In one aspect, the plurality of characteristics may comprise a diameter, a calcification, a lobulation, a spiculation, a volume, and a texture. Upon detection, a malignancy risk score of each nodule may be computed based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules. The plurality of nodules may be classified into AI-confirmed nodules and AI-probable nodules. In one aspect, the AI-confirmed nodules may be classified when the malignancy risk score is greater than a predefined threshold. In the aspect, the AI-probable nodules may be classified when the malignancy risk score is less than or equal to the predefined threshold.

Further, a cursor may be detected the AI-probable nodules. The cursor may be detected based on hovering. Upon detection of the cursor, data associated with each nodule may be displayed. In one aspect, the data may comprise the malignancy score, the lobulation, the spiculation, the diameter and the texture. Subsequently, feedback from a radiologist may be received on a probability of each nodule, a validity of each nodule and the plurality of characteristics of each nodule. In one aspect, the feedback may comprise at least an addition of the AI-probable nodules, a deletion of the AI-confirmed nodules, and an edition of characteristics of the AI-confirmed nodules. Finally, a report may be generated based on the feedback. In one aspect, the report may comprise adapted data associated with the plurality of nodules, thereby adapting the report. In one aspect, the aforementioned method for adapting a report of nodules on the CT scan image may be performed by a processor using programmed instructions stored in a memory.

In another implementation, a non-transitory computer readable medium embodying a program executable in a computing device for adapting a report of nodules in a Computed Tomography (CT) scan image is disclosed. The program may comprise a program code for receiving a CT scan image of a patient. Further, the program may comprise a program code for resampling the CT scan image into a plurality of slices. In one aspect, the CT scan image may be resampled using a bilinear interpolation. Furthermore, the program may comprise a program code for identifying a plurality of region of interests on each slice. In one aspect, each region of interest may be identified using an image processing technique. Subsequently, the program may comprise a program code for detecting a plurality of nodules in the plurality of region of interests using the deep learning. The program may comprise a program code for determining a plurality of characteristics associated with each nodule using the image processing technique. In one aspect, the plurality of characteristics may comprise a diameter, a calcification, a lobulation, a spiculation, a volume, and a texture. The program may further comprise a program code for computing a malignancy risk score of each nodule based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules. The program may comprise a program code for classifying the plurality nodules into AI-confirmed nodules and AI-probable nodules from the plurality of nodules. In one aspect, the AI-confirmed nodules may be classified when the malignancy risk score is greater than a predefined threshold. In the aspect, the AI-probable nodules may be classified when the malignancy risk score is less than or equal to the predefined threshold.

Subsequently, the program may comprise a program code for detecting a cursor on the AI-probable nodules. In one aspect, the cursor may be detected based on hovering. Upon detection of the cursor, the program may comprise a program code for displaying data associated with each nodule.

In one aspect, the data may comprise the malignancy score, the lobulation, the spiculation, the diameter and the texture. The program may further comprise a program code for receiving feedback from a radiologist on a probability of each nodule, a validity of each nodule and the plurality of characteristics of each nodule. In one aspect, the feedback may comprise at least an addition of the AI-probable nodules, a deletion of the AI-confirmed nodules, and an edition of characteristics of the AI-confirmed nodules. Finally, the program may comprise a program code for generating a report based on the feedback. In one aspect, the report may comprise adapted data associated with the plurality of nodules, thereby adapting the report.

BRIEF DESCRIPTION OF THE DRAWINGS

The foregoing detailed description of embodiments is better understood when read in conjunction with the appended drawings. For the purpose of illustrating of the present subject matter, an example of construction of the present subject matter is provided as figures, however, the invention is not limited to the specific method and system for adapting a report of nodules on a CT scan image disclosed in the document and the figures.

The present subject matter is described in detail with reference to the accompanying figures. In the figures, the left-most digit(s) of a reference number identifies the figure in which the reference number first appears. The same numbers are used throughout the drawings to refer various features of the present subject matter.

The figures depict an embodiment of the present disclosure for purposes of illustration only. One skilled in the art will readily recognize from the following discussion that alternative embodiments of the structures and methods illustrated herein may be employed without departing from the principles of the disclosure described herein.

DETAILED DESCRIPTION

Some embodiments of this disclosure, illustrating all its features, will now be discussed in detail. The words "receiving," "resampling," "identifying," "determining," "detecting," "classifying," "displaying," "generating," and other forms thereof, are intended to be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise. Although any system and methods similar or equivalent to those described herein can be used in the practice or testing of embodiments of the present disclosure, the exemplary, system and methods are now described.

The disclosed embodiments are merely examples of the disclosure, which may be embodied in various forms. Various modifications to the embodiment will be readily apparent to those skilled in the art and the generic principles herein may be applied to other embodiments. However, one of ordinary skill in the art will readily recognize that the present disclosure is not intended to be limited to the embodiments described, but is to be accorded the widest scope consistent with the principles and features described herein.

The present subject matter discloses a system and a method for adapting a report of nodules in a CT scan image. Typically, a doctor has to manually identify nodules in the CT scan image. This is a cumbersome and a time-consuming task. More importantly, the present invention discloses a cost effective, efficient, and an automatic process for accurate detection of nodules. The present invention generates a real-time report based on receiving feedback from a radiologist. Further, the present invention provides remote assessment of the CT scan image. Initially, the CT scan image of the patient may be received. Further, a plurality of region of interests may be identified. Furthermore, a plurality of nodules may be detected using deep learning. Subsequently, feedback may be received on the plurality of nodules. Finally, a report may be generated based on the feedback.

While aspects of described system and method for adapting nodules on a Computing Tomography (CT) scan image may be implemented in any number of different computing systems, environments, and/or configurations, the embodiments are described in the context of the following exemplary system.

Figure 1:
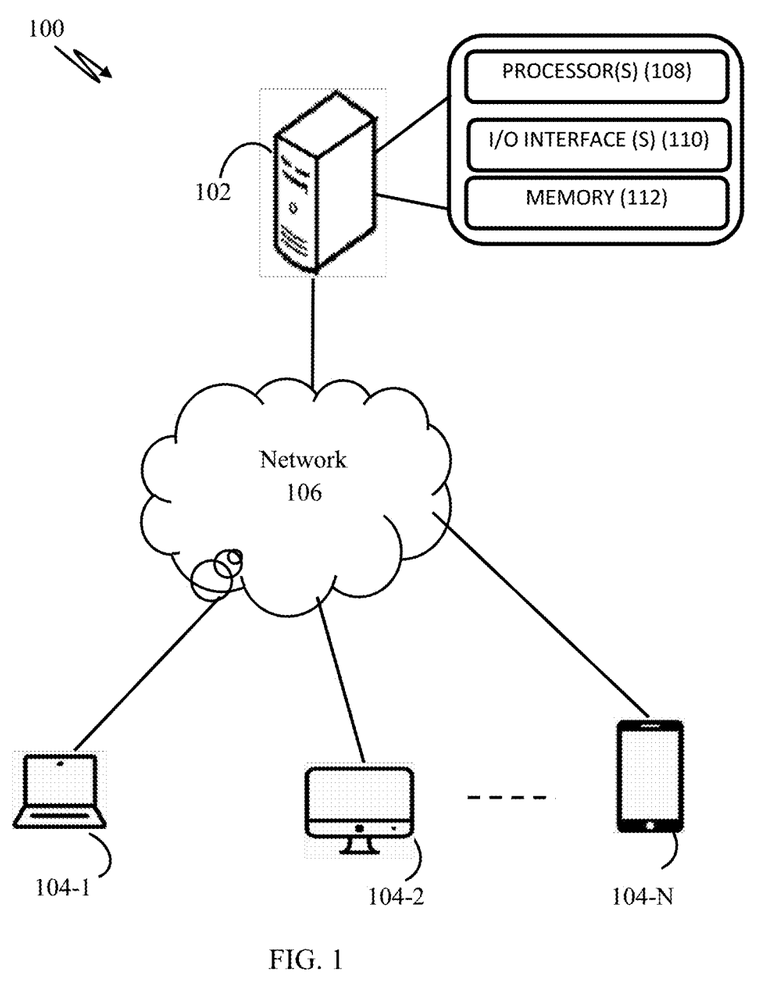
FIG. 1 illustrates a network implementation of a system for adapting a report of nodules in a CT scan image, in accordance with an embodiment of the present subject matter.

Referring now to FIG. 1, a network implementation 100 of a system 102 for adapting a report of nodules in a Computed Tomography (CT) scan image is disclosed. It may be noted that one or more users may access the system 102 through one or more user devices 104-1, 104-2 . . . 104-N, collectively referred to as user devices 104, hereinafter, or applications residing on the user devices 104. In one aspect, the one or more users may comprise a health practitioner, a doctor, a radiologist and the like.

Although the present disclosure is explained considering that the system 102 is implemented on a server, it may be understood that the system 102 may be implemented in a variety of computing systems, such as a laptop computer, a desktop computer, a notebook, a workstation, a virtual environment, a mainframe computer, a server, a network server, a cloud-based computing environment. It will be understood that the system 102 may be accessed by multiple users through one or more user devices 104-1, 104-2 . . . 104-N. In one implementation, the system 102 may comprise the cloud-based computing environment in which the user may operate individual computing systems configured to execute remotely located applications. Examples of the user devices 104 may include, but are not limited to, a portable computer, a personal digital assistant, a handheld device, and a workstation. The user devices 104 are communicatively coupled to the system 102 through a network 106.

In one implementation, the network 106 may be a wireless network, a wired network, or a combination thereof. The network 106 can be implemented as one of the different types of networks, such as intranet, local area network (LAN), wide area network (WAN), the internet, and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 106 may include a variety of network devices, including routers, bridges, servers, computing devices, storage devices, and the like.

In one embodiment, the system 102 may include at least one processor 108, an input/output (I/O) interface 110, and a memory 112. The at least one processor 108 may be implemented as one or more microprocessors, microcomputers, microcontrollers, digital signal processors, Central Processing Units (CPUs), state machines, logic circuitries, and/or any devices that manipulate signals based on operational instructions. Among other capabilities, the at least one processor 108 is configured to fetch and execute computer-readable instructions stored in the memory 112.

The I/O interface 110 may include a variety of software and hardware interfaces, for example, a web interface, a graphical user interface, and the like. The I/O interface 110 may allow the system 102 to interact with the user directly or through the client devices 104. Further, the I/O interface 110 may enable the system 102 to communicate with other computing devices, such as web servers and external data servers (not shown). The I/O interface 110 can facilitate multiple communications within a wide variety of networks and protocol types, including wired networks, for example, LAN, cable, etc., and wireless networks, such as WLAN, cellular, or satellite. The I/O interface 110 may include one or more ports for connecting a number of devices to one another or to another server.

The memory 112 may include any computer-readable medium or computer program product known in the art including, for example, volatile memory, such as static random access memory (SRAM) and dynamic random access memory (DRAM), and/or nonvolatile memory, such as read only memory (ROM), erasable programmable ROM, flash memories, hard disks, Solid State Disks (SSD), optical disks, and magnetic tapes. The memory 112 may include routines, programs, objects, components, data structures, etc., which perform particular tasks or implement particular abstract data types. The memory 112 may include programs or coded instructions that supplement applications and functions of the system 102. In one embodiment, the memory 112, amongst other things, serves as a repository for storing data processed, received, and generated by one or more of the programs or the coded instructions.

As there are various challenges observed in the existing art, the challenges necessitate the need to build the system 102 for adapting the report of nodules on the CT scan image. At first, a user may use the user device 104 to access the system 102 via the I/O interface 110. The user may register the user devices 104 using the I/O interface 110 in order to use the system 102. In one aspect, the user may access the I/O interface 110 of the system 102. The detail functioning of the system 102 is described below with the help of figures.

The present subject matter describes the system 102 for adapting the report of nodules in the CT scan image. The system 102 may adapt the report of the nodules detected on the CT scan image in real-time. The system 102 may use an artificial intelligence technique to adapt the nodules. In order to adapt the nodules on the CT scan image, initially, the system 102 may receive the CT scan image of a patient. In one aspect, the CT scan image may be referred as a chest CT scan. The CT scan image may be a three-dimensional image.

In one aspect, the CT scan image may be a Non-contrast CT series with axial cuts and soft reconstruction kernel which covers an entire Lung. The CT scan image may be one non-contrast CT series with consistently spaced axial slices. The CT scan image may comprise minimum of 40 axial slices in the series. The CT scan image may be available in a Digital Imaging and Communications in Medicine (DICOM) format. In one example, a maximum thickness of the CT scan image may be 6 mm.

In one embodiment, the system 102 may check if the CT scan image is not a Chest CT scan or if there is no plain axial series, then the CT scan image may not be processed further. The system 102 may transmit a response to the user indicating that the uploaded series or the CT scan image is not a valid.

In one embodiment, the system 102 may comprise a trained data model. The trained data model may comprise historical data related to previous CT scans of the patient, one or more CT scans associated with a set of patients and the like. In one example, the trained data model may comprise dataset containing 120,000 Chest CTs used for training and internally validating algorithms. The dataset may be referred to as 'development dataset'. The development dataset may be divided into training dataset and internal validation dataset using a 4:1 split. The resultant validation dataset (20% of the entire data) may be used to estimate the performance of the trained data model and for hyper-parameter tuning. The splitting may be based on a patient identity (ID) eliminating any spillage between the training and the validation splits.

In one aspect, the dataset in the trained data model may be large and valid that results into multiple advantages. The dataset may comprise an adequate number of scans for all target abnormalities, allowing the development of accurate algorithm. An adequate number of control scans with various non-target abnormalities and normal variations may be likely to be present in the dataset. It may reduce the chances that these occurrences will negatively impact performance when the algorithm is deployed in the real world on previously unseen data. The selection of a large number of sources for the training data, rather than a large amount of data from a single site, may be advantageous because it allows the algorithms to be trained on the CT scan images from a wide variety of device manufacturers and CT protocols, without explicitly specifying.

In one embodiment, the system 102 may automate the checking of the DICOM for age, body part, contrast/non-contrast, slice thickness, view, and kernel. The system 102 may use a separate module called a series classifier which is described in detail in the preprocessing section. Further, the system 102 may check presence of a corresponding radiology report i.e., a ground truth, by matching the patient IDs. If no report is found, the CT scan image may be excluded. Subsequently, the system 102 may automate the checking of radiology report for the age. The system 102 may identify a number of cases which are labelled as CHEST in the DICOM attribute but are not actually Chest CT scan images, such CT scan images may be identified using the trained series classifier and not used in training or testing (these can be considered outliers).

In one embodiment, only requirements for training the system 102 may be the presence of the DICOM data and a text report. Once these requirements are met, the concept of missing values or missing data may not apply as it does for other machine learning algorithms. There may be no other exclusions from the training dataset.

In order to eliminate the possibility of data/label leakage, the training and the validation split may be performed using a randomization procedure at the patient level rather than at the Study level. The Chest CT scan image studies from an (de-identified) individual may be placed either in the training set or the testing set, but not both. There may be no train-test contamination as the sources of data that were used for train data are completely different to those used for collecting test data. There may be no validation data contamination as the training and the validation split is done based on the hash of a unique identifier. The input data is an image i.e., the CT scan image whereas the target variable is a binary output i.e., information related to the presence of a particular abnormality is not encoded in the actual image. In one example, an abnormal Chest CT scan image may not have any explicit information that it is abnormal apart from features in the image data.

In one aspect, an automated natural language processing based labeling approach may be chosen as the primary method for generating the ground truth. Additionally, a number of pixel-level hand annotations may be used to either further improve accuracy or to provide input to a segmentation algorithm. It may be noted that an intended use of the system 102 is to aid in the interpretation of the Chest CT images, therefore the labeling method that largely depends on the radiology reports, which are the ground truth for these images, is appropriate.

Each Chest CT scan image in the training dataset may have a single corresponding the ground truth, generated during the normal course of clinical care. The ground truth includes at least the radiology report and a biopsy report where available. The ground truth is used for training the algorithm. The radiologist reports may not be generated specifically for the purpose of training the system 102 but may be obtained retrospectively from anonymized clinical records. The source of the reports may be exactly the same as the source of the CT scan images. In one example, the qualifications of the radiologists who generated these reports may be one of—MD, Radiology: Doctor of Medicine in Radiology, DNB, Radiology: Diplomate of National Board, Radiology, and DMRD: Diploma in Medical Radio Diagnosis.

In one aspect, the report may be in a free text format, and a custom Natural Language Processing (NLP) algorithm may be used to extract labels corresponding to each of the abnormal findings(indications). The labels may be served as the ground truth. The NLP algorithm may use well-established systems developed to manage typographic errors, detect negations and identify synonyms.

The Natural Language Processing (NLP) algorithms may be developed based on rules/dictionaries, trained with machine learning techniques, or a combination of the two approaches. Rule based NLP algorithm may use a list of manually created rules to parse the unorganized content and structure it. Machine Learning (ML) based NLP algorithm, on the other hand, may automatically generate the rules when trained on a large annotated dataset. The rule-based NLP algorithm may be chosen over a machine-learning based NLP algorithm for the purpose of labeling radiology reports.

The rule-based NLP algorithm may have few advantages comprising clinical knowledge can be manually incorporated into the rule-based NLP algorithm. In order to capture this knowledge in the ML based algorithm, a huge amount of annotation may be required. Further, rules may be readily added or modified to accommodate a new set of target findings in the rule-based NLP algorithm.

Once the CT scan image is received, the system 102 may resample the CT scan image into a plurality of slices. The CT scan image may be resampled using a bilinear interpolation. In one aspect, the system 102 may resample the CT scan image so that its slice thickness is around 2.5 mm. The system 102 may obtain a resampling factor by dividing 2.5 by the series' slice thickness and rounding the result to an integer. The rounding may be used to ensure that there are no resampling artifacts.

Further, the system 102 may identify a plurality of region of interests on each slice. The plurality of region of interests may be identified using an image processing technique. In one aspect, each region of interest may indicate an abnormality on each slice. In one example, each region of interest may correspond to possible nodules on each slice.

In one embodiment, a small part of the CT scan image may be annotated at a pixel level which serve as the secondary labels to training algorithms. It may include the region of interest annotation (lung, diaphragm, mediastinum and ribs) as well as abnormality pixel-wise annotation which are then used to derive the Region of Interest (ROI) level annotations. In one example, 5% of the Chest CT scan images may be duplicated, as a test for competency of the annotators. If there is less than 75% concordance the CT scan image is re-annotated. These discrepancies may be tracked as a way to continually test the accuracy of the annotations and the competency of the annotators.

Subsequently, the system 102 may detect a plurality of nodules in each region of interest. The plurality of nodules may be detected using the deep learning. In one example, Convolutional Neural Network (CNN) may be used to detect the plurality of nodules. Further, a total number of slices in which the nodule is present may be computed.

In one aspect, the system 102 may comprise a Se-ResNeXt50 model to detect the plurality of nodules. The Se-ResNeXt50 may be a modified version of ResneXt 50 a popular neural network architecture which has 50 layers with increased inter layer connectivity. The model may have 50 convolutional layers, modified to take in regional information and softmax based confidences. Further, the system 102 may comprise U-Net and Features Pyramid Network (FPN). The U-Net and FPN may be a popular segmentation architecture for biomedical segmentation. The U-Net and FPN may have five downsampling and five upsampling blocks of convolutional layers with skip connections.

In one embodiment, the CNN or ConvNet is a class of deep neural networks, most commonly applied to analyzing visual images. Neural networks may be composed of a large number of interconnected individual computational units, arranged in layers, each of which applies a learned function to the input data. CNN may be used for image processing and may be characterized by 'convolution' layers, which contain layers that learn the matrix operations required to efficiently process images.

Upon detection of the plurality of nodules, the system 102 may determine a plurality of characteristics associated with each nodule. The plurality of characteristics may be determined using an image processing technique. In one aspect, the system 102 may analyze each nodule using the image processing technique. Based on the analysis, the system 102 may determine the plurality of characteristics. The plurality of characteristics may comprise a diameter, a calcification, a lobulation, a spiculation, a texture, a volume and the like.

In one aspect, the diameter may correspond to a size. The calcification may indicate an amount of calcium present. The lobulation may indicate a location. The speculation may indicate a border. In one embodiment, the system 102 may use a Convolution Neural Network (CNN) module to determine the plurality of characteristics.

Further, the system 102 may compute a malignancy risk score for each nodule. The malignancy risk score may be computed based on the plurality of characteristics and the trained data model. The malignancy risk score may indicate if the nodule is malignant i.e., cancerous or not.

In one aspect, the trained data model may comprise historical data related to different diameter of nodules, different calcification of nodules, different lobulation of nodules, different spiculation of nodules, different volume of nodules, different texture of nodules and the like. In one example, the historical data may comprise previous clinical reports associated with a set of patients. The trained data model may be generated based on continuously learning data associated with the set of patients using the deep learning. The trained data model may enable an accurate analysis.

In one embodiment, the system 102 may compare the plurality of characteristics with the historical data. In one aspect, the system 102 may use a Convolutional Neural Network (CNN) model for the comparison. In one example, the diameter may be compared with the different diameter of nodules. The calcification may be compared with the different calcification of nodules. The lobulation may be compared with the different lobulation of nodules. The spiculation may be compared with the different spiculation of nodules. The volume may be compared with the different volume of nodules. The texture may be compared with the different texture of nodules. Based on the comparison, the system 102 may computer the malignancy risk score for the patient. The malignancy risk score may be computed in real-time.

In another embodiment, the system 102 may assign a weightage to each characteristic. Further, the weightage and the plurality of characteristics may be used to compute the malignancy risk score.

Further, the system 102 may classify the plurality of nodules into Artificial Intelligence (AI)-confirmed nodules and Artificial Intelligence (AI)-probable nodules. The plurality of nodules may be classified based on the malignancy risk score and a predefined threshold. In one aspect, the system 102 may compare the malignancy risk score of each nodule with the predefined threshold. Based on the comparison, the system 102 may classify the plurality of nodules. In the aspect, the system 102 may use Convolutional Neural Network (CNN) to compare the malignancy risk score and the predefined threshold.

In one embodiment, the plurality of nodules may be classified using an artificial intelligence technique. The AI-confirmed nodules may be visible nodules. The AI-probable nodules may be invisible nodules. In one example, the AI-confirmed nodules may be probable nodules and the AI-probable nodules may be non-probable nodules. In one aspect, if the malignancy risk score is greater than the predefined threshold, the plurality of nodules may be classified as the AI-confirmed nodules. In another aspect, if the malignancy risk score is less than or equal to the predefined threshold, the plurality of nodules may be classified as the AI-probable nodules.

In one embodiment, the system 102 may classify the plurality of nodules into the AI-confirmed nodules and the AI-probable nodules based on comparison of the diameter of each nodule with a predefined diameter. In the embodiment, if the diameter is greater than the predefined diameter, the plurality of nodules may be classified as the AI-confirmed nodules. If the diameter is less than or equal to the predefined diameter, the plurality of nodules may be classified as the AI-probable nodules.

In one example, construe the predefined threshold as 10. Further, the malignancy score for 5 nodules i.e., nodules-1 may be 7, nodule-2 may be 10, nodule-3 may be 12, nodule-4 may be 15, and nodule-5 may be 3. The nodules with the malignancy score greater than the predefined threshold i.e., nodule-3 and nodule-4 may be classified as the AI-confirmed nodules. Subsequently, the nodules with the malignancy score less than or equal to the predefined threshold i.e., nodule-1, nodule-2 and nodule-5 may be classified as the AI-probable nodules.

Figure 2:
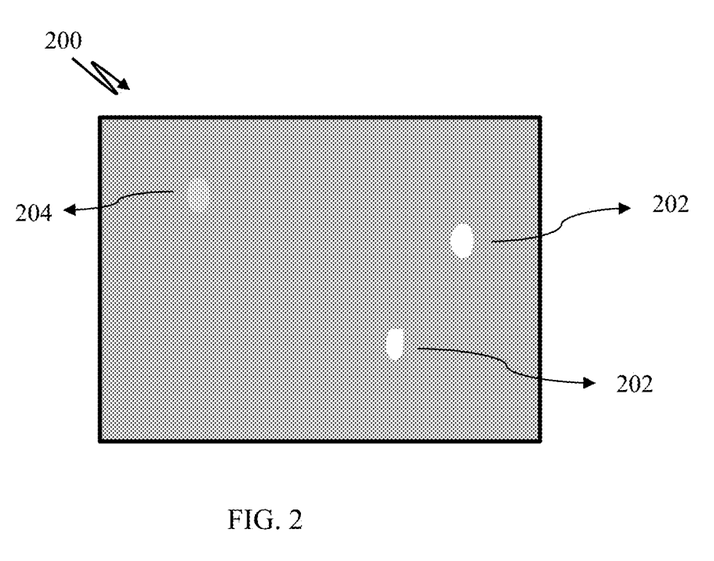
FIG. 2 shows AI-confirmed nodules and AI-probable nodules on the CT scan image, in accordance with an embodiment of the present subject matter.

Referring now to FIG. 2, AI-confirmed nodules and AI-probable nodules on the CT scan image 200 is shown, in an embodiment of the present subject matter. In one embodiment, the malignancy score of the nodules 202 may be greater than the predefined threshold. The nodules 202 may be the AI-confirmed nodules. In the embodiment, the malignancy score of the nodule 204 may be less than or equal to the predefined threshold. The nodule 204 may be the AI-probable nodule.

Referring again to the FIG. 1, upon classification, the system 102 may detect a cursor on the AI-probable nodules. The cursor may be detected based on hovering on each nodule. The system 102 may display data associated with each nodule upon detection of the cursor. The data may comprise the plurality of nodules, the malignancy score associated with each nodule, the plurality of characteristics such as the diameter, the texture, the lobulation, the spiculation, and the like. In one embodiment, the data associated with the AI-confirmed nodules may be already displayed. The AI-probable nodules may be hidden and are shown after a click of cursor on it is detected.

In one aspect, the AI-probable nodules may be popped up upon hovering the cursor. The system 102 may further display the data of the non-probable nodules.

Further, the system 102 may receive feedback from a radiologist. The feedback may be received on a probability of each nodule, a validity of each nodule and the plurality of characteristics of each nodule. The feedback may comprise an addition of the AI-probable nodules, a deletion of the AI-confirmed nodules, a confirmation of each nodule, an edition of characteristics of the AI-confirmed nodules and the like. The confirmation of each nodule may be refereed as the confirmation on the AI-confirmed nodules or the AI-probable nodules. The edition of characteristics may comprise editing one or more characteristics of the AI-confirmed nodules.

In one aspect, the addition of the AI-probable nodules may indicate that one of the AI-probable nodules may be added as the AI-confirmed nodules. In another aspect, the deletion of the AI-confirmed nodules may indicate that one of the AI-confirmed nodules may be added as the AI-probable nodules. In yet another aspect, the confirmation may indicate that the AI-confirmed nodules and the AI-probable nodules are classified correctly.

In one embodiment, the system 102 may transmit the data associated with the plurality of nodules to the radiologist. Upon transmission, the feedback may be received from the radiologist.

Once the feedback is received, the system 102 may generate a report. The report may comprise adapted data associated with the plurality of nodules. In one aspect, the adapted data of the AI-confirmed nodules may be present in the report. The adapted data of the AI-confirmed nodules may be further used for further analysis. In one embodiment, the system 102 may modify or adapt the data based on the feedback. Upon adaption, the data may be referred as the adapted data. The adapted data may be associated with the plurality of nodules. In one aspect, the report may comprise the diameter, the texture, the lobulation, the spiculation, the malignancy score associated with the probable nodules and the like.

The report may be used for further process. The report may be shared with the patient and a health practitioner. The report may be updated based on the feedback. In one aspect, the system 102 may analyze the report. Based on the analysis, the system 102 may schedule an appointment for the patient with the health practitioner.

In one embodiment, the system 102 may train the trained data model and a successive model based on the feedback. The system may use a supervised learning technique for training. In the embodiment, the system 102 may learn from the feedback, and provide accurate classification of the AI-confirmed nodules and the AI-probable nodules in future.

In one embodiment, the system 102 may be an adaptable artificial intelligence system. The system 102 classifies the plurality of nodules using the artificial intelligence technique. Further, the system 102 receives feedback on the probability of each nodule, the validity of each nodule and the plurality of characteristics of each nodule. Based on the feedback, the system 102 may adapt the data related to the plurality of nodules. Further, the report comprising the adapted data may be generated.

In one embodiment, the system 102 may receive an X-radiation (X-ray) image of a patient. The system 102 may detect the plurality of nodules in the X-ray image. Further, the system 102 may determine the plurality of characteristics associated with each nodule. Furthermore, the system 102 may generate the malignancy risk score for each nodule. The malignancy risk score may be compared with the predefined threshold. Based on the comparison, the system 102 may classify the plurality of nodules into the AI-confirmed nodules and the AI-probable nodules. The system 102 may receive feedback on the probability of the nodules, the validity of nodules and the plurality of characteristics. Based on the feedback, the system 102 may update the data associated with the nodules. The system 102 may generate the report comprising the adapted data of the plurality of nodules.

Figure 3:
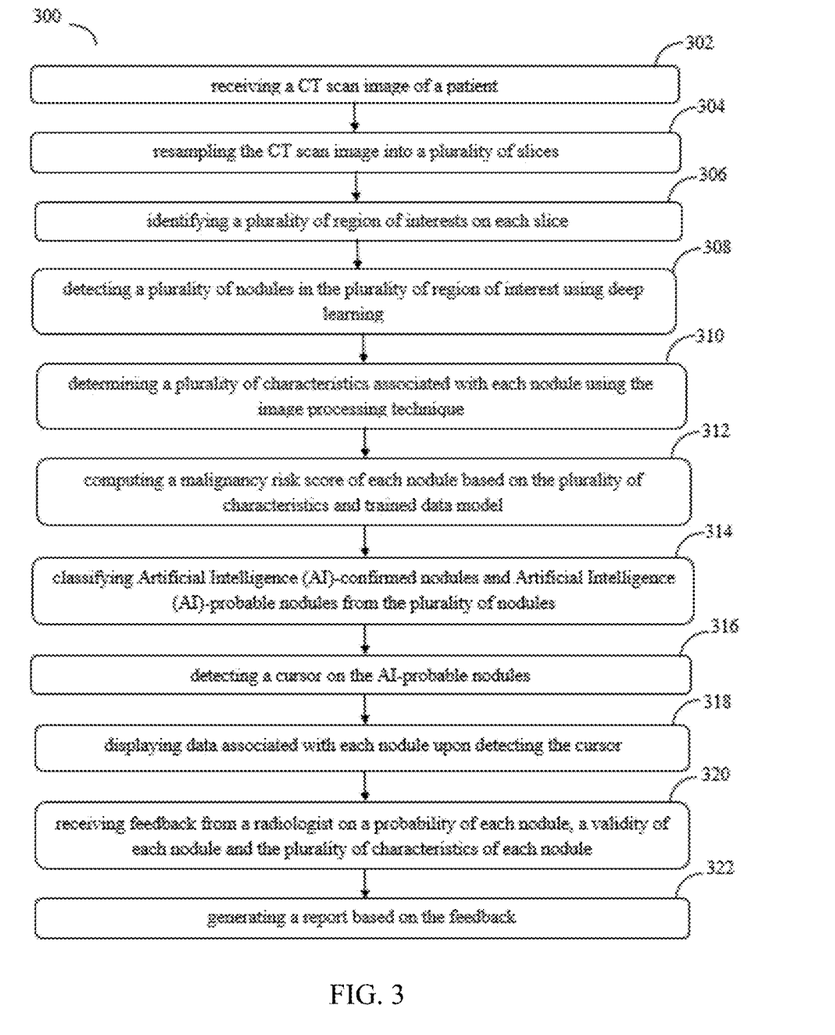
FIG. 3 illustrates a method for adapting a report of nodules in a CT scan image, in accordance with an embodiment of the present subject matter.

Referring now to FIG. 3, a method 300 for adapting a report of nodules on computed tomography (CT) scan image is shown, in accordance with an embodiment of the present subject matter. The method 300 may be described in the general context of computer executable instructions. Generally, computer executable instructions can include routines, programs, objects, components, data structures, procedures, modules, functions, etc., that perform particular functions or implement particular abstract data types.

The order in which the method 300 is described is not intended to be construed as a limitation, and any number of the described method blocks can be combined in any order to implement the method 300 or alternate methods for adapting the report of nodules on the CT scan image. Additionally, individual blocks may be deleted from the method 300 without departing from the spirit and scope of the subject matter described herein. Furthermore, the method 300 for adapting the report of nodules on CT scan image can be implemented in any suitable hardware, software, firmware, or combination thereof. However, for ease of explanation, in the embodiments described below, the method 300 may be considered to be implemented in the above-described system 102.

At block 302, a CT scan image of a patient may be received.

At block 304, the CT scan image may be resampled into a plurality of slices. In one aspect, the CT scan image may be resampled using a bilinear interpolation.

At block 306, a plurality of region of interests may be identified. In one aspect, the plurality of region of interests may be identified using an image processing technique.

At block 308, a plurality of nodules in the plurality of region of interests may be detected using the deep learning.

At block 310, a plurality of characteristics associated with each nodule may be determined using the image processing technique. In one aspect, the plurality of characteristics may comprise a diameter, a calcification, a lobulation, a spiculation, a volume and a texture.

At block 312, a malignancy risk score of each nodule may be computed based on the plurality of characteristics and trained data model. In one aspect, the trained data model may comprise historical data related to different diameter of nodules, different calcification of nodules, different lobulation of nodules, different spiculation of nodules, different volume of nodules, and different texture of nodules.

At block 314, AI-confirmed nodules and AI-probable nodules may be classified from the plurality of nodules. In one aspect, the AI-confirmed nodules may be classified when the malignancy risk score is greater than a predefined threshold. In the aspect, the AI-probable nodules may be classified when the malignancy risk score is less than or equal to the predefined threshold.

At block 316, a cursor may be detected on the AT-probable nodules. In one aspect, the cursor may be detected based on hovering.

At block 318, data associated with each nodule may be upon detecting the cursor. In one aspect, the data may comprise the malignancy score, the lobulation, the spiculation, the diameter and the texture.

At block 320, feedback from a radiologist may be received on a probability of each nodule, a validity of each nodule and the plurality of characteristics of each nodule. In one aspect, the feedback may comprise at least an addition of the AI-probable nodules and a deletion of the AI-confirmed nodules.

At block 322, a report may be generated based on the feedback. In one aspect, the report may comprise adapted data associated with the plurality of nodules.

Exemplary embodiments discussed above may provide certain advantages. Though not required to practice aspects of the disclosure, these advantages may include those provided by the following features.

Some embodiments of the system and the method enable annotating nodules on a CT scan image using artificial intelligence technique.

Some embodiments of the system and the method enable receiving feedback on the nodules on the CT scan image.

Some embodiments of the system and the method enable adapting data associated with nodules in real-time based on the feedback.

Some embodiments of the system and the method enable accurately detecting the nodules on the CT scan image.

Some embodiments of the system and the method enable an efficient and fast process.

Although implementations for methods and system for adapting a report of nodules in a CT scan image have been described in language specific to structural features and/or methods, it is to be understood that the appended claims are not necessarily limited to the specific features or methods described. Rather, the specific features and methods are disclosed as examples of implementations for adapting the report of nodules in the CT scan image.

What is claimed is:

1. A method for adapting a report of nodules in a CT scan image, the method comprises:
   receiving, by a processor (108), a CT scan image of a patient;
   resampling, by the processor (108), the CT scan image into a plurality of slices, wherein the CT scan image is resampled using a bilinear interpolation;
   identifying, by the processor (108), a plurality of region of interests on each slice, wherein each region of interest is identified using an image processing technique;
   detecting, by the processor (108), a plurality of nodules in the plurality of region of interests using the deep learning;
   determining, by the processor (108), a plurality of characteristics associated with each nodule using the image processing technique, wherein the plurality of characteristics comprise a diameter, a calcification, a lobulation, a spiculation, a volume and a texture;
   computing, by the processor (108), a malignancy risk score of each nodule based on the plurality of characteristics and trained data model, wherein the trained data model comprises historical data related to different diameter of nodules, different calcification of nodules, different lobulation of nodules, different spiculation of nodules, different volume of nodules, and different texture of nodules;
   classifying, by the processor (108), Artificial Intelligence (AI)-confirmed nodules and Artificial Intelligence (AI)-probable nodules from the plurality of nodules, wherein the AI-confirmed nodules are classified when the malignancy risk score is greater than a predefined threshold, and wherein the AI-probable nodules are classified when the malignancy risk score is less than or equal to the predefined threshold;
   detecting, by the processor (108), a cursor on the AI-probable nodules, wherein the cursor is detected based on hovering;
   displaying, by the processor (108), data associated with each nodule upon detecting the cursor, wherein the data comprises the malignancy score, the lobulation, the spiculation, the diameter and the texture;
   receiving, by the processor (108), feedback from a radiologist on a probability of each nodule, a validity of each nodule and the plurality of characteristics of each nodule, wherein the feedback comprises at least an addition of the AI-probable nodules, a deletion of the AI-confirmed nodules, and an edition of characteristics of the AI-confirmed nodules; and
   generating, by the processor (108), a report based on the feedback, wherein the report comprises adapted data associated with the plurality of nodules, thereby adapting the report.

2. The method as claimed in claim 1, further comprises transmitting the data associated with the plurality of nodules to the radiologist, wherein the data comprises the plurality of nodules, the malignancy score associated with each nodule and the plurality of characteristics.

3. The method as claimed in claim 1, further comprises receiving the feedback on a confirmation on each nodule from the radiologist based on the probability of each nodule, a validity of each nodule and the plurality of characteristics of each nodule.

4. The method as claimed in claim 1, further comprises training the trained data model and a successive model based on the feedback using a supervised learning technique.

5. The method as claimed in claim 1, further comprises classifying the AI-confirmed nodules and the AI-probable nodules using an artificial intelligence technique.

6. The method as claimed in claim 1, further comprises popping-up the AI-probable nodules upon detection of the cursor.

7. A system (102) for adapting a report of nodules in a CT scan image, the system comprises:
   a memory (112); and
   a processor (108) coupled to the memory (112), wherein the processor (108) is configured to execute instructions stored in the memory (112) to:
   receive a CT scan image of a patient;
   resample the CT scan image into a plurality of slices, wherein the CT scan image is resampled using a bilinear interpolation;
   identify a plurality of region of interests on each slice, wherein each region of interest is identified using an image processing technique;
   detect a plurality of nodules in the plurality of region of interests using the deep learning;
   determine a plurality of characteristics associated with each nodule using the image processing technique, wherein the plurality of characteristics comprise a diameter, a calcification, a lobulation, a spiculation, a volume and a texture;
   compute a malignancy risk score of each nodule based on the plurality of characteristics and trained data model, wherein the trained data model comprises historical data related to different diameter of nodules, different calcification of nodules, different lobulation of nodules, different spiculation of nodules, different volume of nodules, and different texture of nodules;
   classify AI-confirmed nodules and AI-probable nodules from the plurality of nodules, wherein the AI-confirmed nodules are classified when the malignancy risk score is greater than a predefined threshold, and wherein the AI-probable nodules are classified when the malignancy risk score is less than or equal to the predefined threshold;
   detect a cursor on the AI-probable nodules, wherein the cursor is detected based on hovering;
   display data associated with each nodule upon detecting the cursor, wherein the data comprises the malignancy score, the lobulation, the spiculation, the diameter and the texture;
   receive feedback from a radiologist on a probability of each nodule, a validity of each nodule and the plurality of characteristics of each nodule, wherein the feedback comprises at least an addition of the AI-probable nodules, a deletion of the AI-confirmed nodules and an edition of characteristics of the AI-confirmed nodules; and
   generate a report based on the feedback, wherein the report comprises adapted data associated with the plurality of nodules, thereby adapting the report.

8. The system (102) as claimed in claim 7, further configured to transmit the data associated with the plurality of nodules to the radiologist, wherein the data comprises the plurality of nodules, the malignancy score associated with each nodule and the plurality of characteristics.

9. The system (102) as claimed in claim 7, further configured to receive the feedback on a confirmation on each nodule from the radiologist based on the probability of each nodule, a validity of each nodule and the plurality of characteristics of each nodule.

10. The system as (102) claimed in claim 7, further configured to train the trained data model and a successive model based on the feedback using a supervised learning technique.

11. The system (102) as claimed in claim 7, further configured to classify the AI-confirmed nodules and the AI-probable nodules using an artificial intelligence technique.

12. The system (102) as claimed in claim 7, further configured to pop-up the non-probable nodules upon detection of the cursor.

13. A non-transitory computer program product having embodied thereon a computer program for adapting a report of nodules in a Computed Tomography (CT) scan image, the computer program product storing instructions, the instructions comprising instructions for:

receiving a CT scan image of a patient;

resampling the CT scan image into a plurality of slices, wherein the CT scan image is resampled using a bilinear interpolation;

identifying a plurality of region of interests on each slice, wherein each region of interest is identified using an image processing technique;

detecting a plurality of nodules in the plurality of region of interests using the deep learning;

determining a plurality of characteristics associated with nodule using the image processing technique, wherein the plurality of characteristics comprise a diameter, a calcification, a lobulation, a spiculation, a volume, and a texture;

computing a malignancy risk score of each nodule based on the plurality of characteristics and trained data model, wherein the trained data model comprises historical data related to different diameter of nodules, different calcification of nodules, different lobulation of nodules, different spiculation of nodules, different volume of nodules, and different texture of nodules;

classifying AI-confirmed nodules and AI-probable nodules from the plurality of nodules, wherein the AI-confirmed nodules are classified when the malignancy risk score is greater than a predefined threshold, and wherein the AI-probable nodules are classified when the malignancy risk score is less than or equal to the predefined threshold;

detecting a cursor on the AI-probable nodules, wherein the cursor is detected based on hovering;

displaying data associated with each nodule upon detecting the cursor, wherein the data comprises the malignancy score, the lobulation, the spiculation, the diameter and the texture;

receiving feedback from a radiologist on a probability of each nodule, a validity of each nodule and the plurality of characteristics of each nodule, wherein the feedback comprises at least an addition of the AI-probable nodules, a deletion of the AI-confirmed nodules, and an edition of characteristics of the AI-confirmed nodules; and generating a report based on the feedback, wherein the report comprises adapted data associated with the plurality of nodules, thereby adapting the report.

* * * * *